United States Patent [19]

Williams, Jr.

[11] 4,447,630

[45] May 8, 1984

[54] METHOD FOR MAKING CYCLOPOLYDIMETHYLSILOXANES

[75] Inventor: Robert E. Williams, Jr., Scotia, N.Y.

[73] Assignee: General Electric Company, Schenectady, N.Y.

[21] Appl. No.: 527,539

[22] Filed: Aug. 29, 1983

[51] Int. Cl.$^3$ ............................................... C07F 7/08
[52] U.S. Cl. ..................................................... 556/460
[58] Field of Search ......................................... 556/460

[56] References Cited

U.S. PATENT DOCUMENTS 2,465,547 3/1949 McGregor et al. ................. 556/460
2,732,398 1/1956 Brice et al. .
3,983,148 9/1976 Reedy et al. .

FOREIGN PATENT DOCUMENTS 887659 12/1971 Canada ............................... 556/460

Primary Examiner—Paul F. Shaver
Attorney, Agent, or Firm—William A. Teoli; James C. Davis, Jr.; James Magee, Jr.

[57] ABSTRACT

A method is provided for making cyclopolysiloxanes by hydrolyzing diorganodichlorosilanes and aqueous hydrochloric acid in the presence of an effective amount of a perfluorinated alkyl substituted organic material, such as a perfluorinated alkyl sulfonic acid salt.

4 Claims, No Drawings

METHOD FOR MAKING CYCLOPOLYDIMETHYLSILOXANES

CROSS REFERENCE TO RELATED APPLICATIONS

Reference is made to my copending application Ser. No. 408,103, now U.S. Pat. No. 4,412,080, filed Aug. 16, 1982, for Methods for Preparing Cyclopolysiloxanes and Ser. No. 412,062, now U.S. Pat. No. 4,412,081, filed Aug. 27, 1982, for Method for preparing Decamethylcyclopentasiloxane, where both applications are assigned to the same assignee as the present invention and incorporated herein by reference.

BACKGROUND OF THE INVENTION

Prior to the present invention, cyclopolydimethylsiloxanes were prepared by hydrolyzing dimethyldichlorosilane in the presence of an effective amount of cationic surface active agent such as a protonated amine or a quaternary ammonium salt, or a protonated quaternary phosphonium salt. As shown by Reedy et al, U.S. Pat. No. 3,983,148, the cationic surface agent, which is essentially soluble only in the aqueous phase, is selected from a limited class of salts of protonated compounds. In addition, Reedy et al's catalysts are subject to acid catalyzed elimination reactions which form products capable of dissolving in and contaminating the resulting cyclopolydimethylsiloxanes.

In my copending application Ser. No. 408,103, cyclic polydimethylsiloxane is described having the formula, $$[(CH_3)_2SiO]_m \quad (1)$$

where m is a whole number equal to from 3-6 inclusive. These cyclics can be made by hydrolyzing dimethyldichlorosilane in the presence of an n-$C_{(6-16)}$ alkyl sulfonic acid. The amount of alkyl sulfonic acid which can be utilized as a hydrolysis catalyst can vary from about 0.1% to about 2% by weight based on the weight of aqueous HCl hydrolysis medium. In instances where the tetramer is desired, where n formula (1) is equal to 4, it has been found that from about 0.25% to 2% by weight, based on the weight of aqueous HCl of alkyl sulfonic acid catalyst will provide effective results.

The present invention is based on my discovery that further improvements in making cyclopolydimethylsiloxanes of formula (1) can be realized if a perfluoroalkylsulfonic acid catalyst is used in place of the aforementioned alkylsulfonic acid. I have found for example, that perfluoroalkylsulfonic acid salts having the formula, $$(C_xF_{2x+1})SO_3M \quad (2)$$

where M is an alkali metal such as potassium, sodium, lithium, or a tetralkylammonium radical, and x is an integer having a value of 6 to 16, can be utilized to make cyclic polydimethylsiloxane of formula (1) at concentrations below 0.1% weight based on the weight of the aqueous HCl hydrolysis medium. Preferably, the perfluoroalkylsulfonic acid of formula (2) can be used at 200 ppm to about 600 ppm based on HCL hydrolysis medium weight. Surprisingly, octamethylcyclotetrasiloxane or "tetramer" can be made in yields as high as 79% by weight based on the weight of the product mixture when utilizing the perfluoroalkylsulfonic acid catalyst at 400 ppm based on the weight of the aqueous HCl hydrolysis medium which can be at concentrations as high as 36% HCl by weight.

STATEMENT OF THE INVENTION

There is provided by the present invention a method for making cyclopolydimethylsiloxanes of formula (1) which comprises,
(A) hydrolyzing dimethyldichlorosilane in an aqueous reaction medium in the presence of an effective amount of a perfluoroalkylsulfonic acid of formula (2) and
(B) recovering the cyclopolydimethylsiloxane from the mixture of (A).

Among the perfluorinated alkyl sulfonic acid salts which can be utilized in the practice of the present invention as hydrolysis catalysts are compounds, such as, $$CF_3(CF_2)_7-SO_3K$$

$$CF_3(CF_2)_9-SO_3K$$

A mixture of perfluorinated C-8 to C-10 alkyl sulfonic acid salts is available commercially from Minnesota Mining and Manufacturing Company under the trade name Fluorad FC-95 fluorocarbon surfactant. In addition to fluoroalkylsulfonic acids there also can be utilized perfluorinated quaternary ammonium salts, and perfluorinated alcohols. Methods for making such fluorocarbon sulfonic acid salt are shown by Trott, U.S. Pat. No. 2,732,398, which is incorporated herein by reference.

The cyclopolysiloxanes made in accordance with the practice of the present invention can be used to make silicone rubbers and silicone fluids. These cyclics also can be used as foam suppressors in particular applications.

Dimethyldichlorosilane can be readily hydrolyzed with water in the presence of the perfluorinated alkylsulfonic acid which can be utilized at from about 100-900 ppm based on the weight of the aqueous hydrolysis medium. The perfluorinated alkylsulfonic acids can be used as a free acid or in the form of an alkali metal salt such as a potassium salt.

Removal of residual HCl from the methylsiloxane is readily accomplished by stirring the methylsiloxanes with an aqueous solution of alkali metal carbonate or bicarbonate, such as sodium carbonate or sodium bicarbonate to effect the neutralization of the HCl to the alkali metal chloride. Subsequent phase separation yields the methylsiloxane with very low chloride values, suitable for further processing. Unlike protonated cationic surfactants of the prior art, such as Reedy et al, which are predominately soluble in the aqueous hydrolysis medium and which are to a limited degree contained in the methylsiloxane hydrolysis products and carried into the neutralization step, the perfluorinated alkylsulfonic acids of the present invention are not neutralized by a base treatment and are more likely to remain in the aqueous medium.

The amount of water in the aqueous HCl which is used with the dimethyldichlorosilane can range from 2 to 30 moles or more of water per mole of silane and should be sufficient at least to hydrolyze all the silicon-bonded chlorine. Generally, I have found that using about 10 to 20 moles of water (in the aqueous HCl) per mole of dimethyldichlorosilane is sufficient to yield large amounts of cyclics of formula (1) In addition, within these limitations as far as the amount of water which is used with the dimethyldichlorosilane is concerned, often there is a direct evolution of HCl (especially when using 36% HCl) resulting in recovery of anhydrous HCl from the hydrolysis reactor. The HCl concentration in the water should range from about 20% to 36% HCl or saturated aqueous HCl.

The temperature at which the reaction is carried out should be carefully monitored between 0° to 100° C., preferably between 30° to 90° C. The mean liquid residence time of the aqueous HCl and the chlorosilane while the hydrolysis reaction is taking place (advantageously with good mixing) is varied widely and is of the order of about 10 minutes to 1 hour, depending on whether the tetramer or pentamer is desired.

In order that those skilled in the art will be better able to practice the invention, the following examples are given by way of illustration and not by way of limitation. All parts are by weight.

EXAMPLE 1

A mixture of C-8 and C-10 perfluoroalkylsulfonic acids, Fluorad FC-95 surfactant, manufactured by the 3M Company of Minneapolis, Minn., was added to 200 grams of a 20%–36% aqueous hydrochloric acid at 60° C. while the resulting mixture was stirred. There was then added dropwise to the resulting stirred aqueous hydrochloric acid mixture, 100 grams of dimethyldichlorosilane over a period of 20–30 minutes. Hydrolysis of the dimethyldichlorosilane in the aqueous hydrochloric acid was continued for several hours and the dimethyldichlorosilane hydrolyzate was then analyzed by VPC with n-nonane as the internal standard. The following results were obtained, where $D_3$ is hexamethylcyclotrisiloxane, $D_4$ is octamethylcyclotetrasiloxane, $D_5$ is decamethylcyclopentasiloxane and $D_6$ is dodecylcyclohexasiloxane:

TABLE I

| % HCl | FC-95 | Time/Temp | % $D_3$ | % $D_4$ | % $D_5$ | % $D_6$ | % Cyclics |
|---|---|---|---|---|---|---|---|
| 200 g/36% | 400 ppm | 60° C./0.5 h | — | 79 | 16 | 3 | 95 |
| 200 g/20% | 200 ppm | 60° C./0.5 h | — | 78 | 17 | 3 | 97 |
| 200 g/36% | None | 60° C./0.5h | — | 53 | 13 | 2 | 70 |

The above results show that the perfluoroalkylsulfonic acid used in the practice of the present invention as a surfactant can provide high yields of octamethylcyclotetrasiloxane at concentrations significantly lower than required by the use of surfactants of the prior art. As a result, incidents of contamination of the desired cyclic siloxanes with surfactant by-products resulting from surfactant breakdown are significantly reduced.

It was further found that the perfluorinatedalkyl sulfonic acids used in the practice of the present invention, were also effective as catalysts for the equilibration of $D_4$ and $D_5$.

Although the above example is directed to only a few of the very many variables which can be utilized in the practice of the method of the present invention, it should be understood that the present invention is directed to the use of a much broader variety of perfluoroalkyl substituted sulfonic acids to achieve improved yields of cyclomethylpolysiloxanes resulting from the hydrolysis of dimethyldichlorosilane in hydrochloric acid.

What I claim as new and desire to secure by Letters Patent of the United States is:

1. A method for making cyclopolydimethylsiloxanes of the formula $$[(CH_3)_2SiO]_m$$

which comprises, (A) hydrolyzing dimethyldichlorosilane in an aqueous reaction medium in the presence of an effective amount of a perfluoroalkyl sulfonic acid salts of the formula $$(C_xF_{2x+1})SO_3M$$

and (B) recovering the cyclopolydimethylsiloxane from the mixture of (A), where M is an alkali metal, or a tetralkylammonium radical, x is 6 to 16 and m is a whole number equal to from 3–6 inclusive.

2. A method in accordance with claim 1, where the cyclopolydimethylsiloxane is octamethylcyclotetrasiloxane.

3. A method in accordance with claim 1, where the perfluoroalkylsulfonic acid is a mixture of C-8 to C-10 potassium salts.

4. A method for making decamethylcyclopentasiloxane by equilibrating octamethylcyclotetrasiloxane in the presence of an effective amount of a perfluoroalkylsulfonic acid having the formula, $$(C_xF_{2x+1})SO_3M$$

where M is an alkali metal such as potassium, sodium, lithium, or a tetralkylammonium radical, and x is an integer having a value of 6 to 16.

* * * * *